(12) United States Patent
Gately

(10) Patent No.: US 6,489,526 B2
(45) Date of Patent: Dec. 3, 2002

(54) METHOD FOR SYNTHESIS OF HYDROCARBYL BRIDGED INDENES

(75) Inventor: Daniel A. Gately, Berthoud, CO (US)

(73) Assignee: Boulder Scientific Company, Mead, CO (US)

( * ) Notice: Subject to any disclaimer, the term of this patent is extended or adjusted under 35 U.S.C. 154(b) by 0 days.

(21) Appl. No.: 10/083,830

(22) Filed: Feb. 27, 2002

(65) Prior Publication Data

US 2002/0107425 A1 Aug. 8, 2002

Related U.S. Application Data

(63) Continuation-in-part of application No. 09/234,481, filed on Jan. 21, 1999.

(51) Int. Cl.$^7$ ............................................. C07C 13/465
(52) U.S. Cl. ....................................................... 585/27
(58) Field of Search ........................... 585/27, 422, 426, 585/360, 478, 479

(56) References Cited

U.S. PATENT DOCUMENTS 5,866,706 A  *  2/1999  Gately ........................ 585/27
6,291,699 B1 *  9/2001  Birmingham et al. ......... 585/27

* cited by examiner

Primary Examiner—Paul F. Shaver
(74) Attorney, Agent, or Firm—Edward S. Irons

(57) ABSTRACT

A method for treating a terminal dihalo hydrocarbyl compound with an alkali metal indenide to produce a bis (indenyl) hydrocarbyl compound is described.

4 Claims, No Drawings

METHOD FOR SYNTHESIS OF HYDROCARBYL BRIDGED INDENES

RELATED APPLICATION

This application is a continuation-in-part of U.S. application Ser. No. 09/234,481 filed Jan. 21, 1999 which describes the treatment of indene lithenides with dibromoethane to produce 1,2-bis(indenyl) ethanes.

FIELD OF THE INVENTION

This invention relates to the synthesis of hydrocarbyl-bridged indenes.

DEFINITION

Hydrocarbyl Bridged Indene—means collectively all isomers of a compound of Formula I:

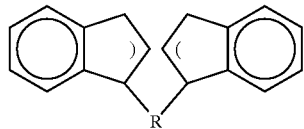

FORMULA I wherein "R" is a hydrocarbyl group.

1,2-bis(indenyl)ethane or EBI—means collectively all isomers of Formula II:

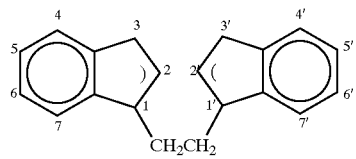

FORMULA II in which the symbol "(" indicates a 1,2-bis(indenyl-1)ethane which has a 1,2, 1,2' double bond (thermodynamic EBI, BRN No. 3055002, CAS RN No. 18657-57-3) or a 2,3 2',3' double bond (kinetic EBI, BRN No. 3083835, CAS RN Nos. 15721-07-0, 18686-04-9, 18686-05-0). atoms are asymmetric when substituted.

Each of the ring substituents may be hydrogen or any one to ten carbon atom hydrocarbyl group. Each ring substituent may be the same as or different from any other ring substituent. One to ten carbon atom alkyl groups are preferred. 2,2' methyl and 4,7, 4'7' dimethyl EBIs are representative.

BACKGROUND OF THE INVENTION

Meso and rac (racemic) forms of kinetic EBI and thermal isomerization of kinetic to thermodynamic EBI are known phenomena. Maréchal, et al, *Bulletin de la Societe Chimique de France* (1967) 8:2954–2961.

Kinetic and thermodynamic EBI are interchangeably useful separately and in mixtures as ligands for metallocene olefin polymerization catalysts. However, the large-scale production of kinetic EBI is constrained because the thermodynamic isomer is produced at temperatures below about −70° C.; whereas, at higher temperatures low yields of kinetic EBI consequent from Spiro indene and vinylindene impurities may result. See, e.g., Yang, et al., *SYNLETT* (1996) 147 and Collins, et al., *J. Organometallic Chem.* (1988) 342:21 (thermodynamic EBI synthesized at −78° C. stirred overnight and warmed to room temperature). See also Ewen, J., et al., *J.Am.Chem.Soc.* (1987) 109:6544–6545 and Grossman, R., et al., *Organometallics* (1991) 10:1501–1505 (50% to 80% recrystallized yields of thermodynamic isomer because of the formation of spiroindene by-product).

SUMMARY OF THE INVENTION

This invention provides a method for the synthesis of 1,2-bis(indenyl) hydrocarbyl compounds, typically 1,2-bis (indenyl) alkanes. Pursuant to one aspect of the invention, an indenyl lithenide is treated with a terminal dihaloalkane and tetrahydrofuran (THF) wherein a reaction mixture containing a hydrocarbyl bridged indene is produced. The reaction is illustrated by Equation 1:

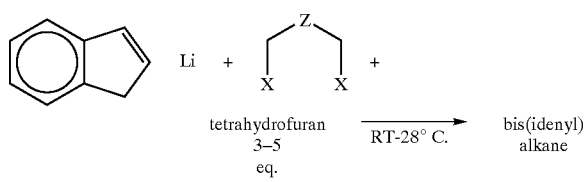

Equation 1

DESCRIPTION OF THE INVENTION

In general, the synthesis of hydrocarbyl bridged indenes pursuant to this invention may be accomplished by treating an indenyl alkali metalide compounds of formula XZX, in which Z is any hydrocarbyl and X is any halogen, e.g., chlorine, preferably in a non-interfering medium, preferably diethyl ether and THF. Preferably, Z is —$(CH_2)_n$—; n=1–20.

The indenyl alkali metalide is prepared treating indene with an alkali metal alkyl in an ether medium at a temperature of −10 to −20° C. Alkali metal alkyls useful in this invention have the formula MOR, wherein M is any alkali metal and R is an alkyl group, typically a $C_1$ to $C_{10}$ alkyl group. N-butyllithium is preferred.

The alkali metalide synthesis reaction mixture typically comprises the selected alkali metal alkyl and the ether medium in which it is produced. Hydrocarbyl bridged indenes may be produced by combining a selected terminal dibromoalkane and THF with an appropriate metalide synthesis reaction mixture. Alternatively, the alkali metalide may first be isolated from the reaction mixture in which it is synthesized. According to one embodiment of the invention, the isolated indenide alkali metalide and THF are then reacted with a dibromoalkane, typically at room temperature, wherein a reaction mixture containing a hydrocarbyl bridged indene is produced. No reaction occurs upon combination of the dibromoalkane with the alkali metalide reaction mixture in ethyl ether.

EXEMPLIFICATION OF THE INVENTION

EXAMPLE 1 (LABORATORY)

Indene in diethyl ether (1.25 equivalents) was treated with BuLi in ethyl ether at −20° C. to provide reaction mixture containing lithium indenide pursuant to Equation 2:

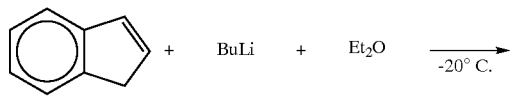

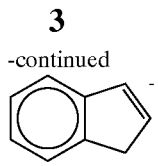

Equation 2

The lithium indenide containing reaction mixture was warmed to room temperature, was stirred for one hour, and then treated 0.5 mol of with dibromoethane. Ten minutes later, THF (0.25 equiv.) was added. The temperature of the reaction slowly warmed to 40° C.

The $^1$H NMR of the product mixture showed >95% yield from indene of the kinetic isomer of EBI. No spiro product was observed. See Equation 3:

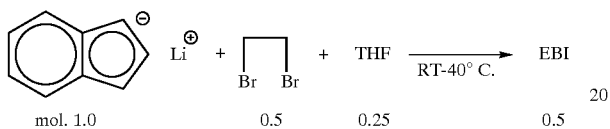

Equation 3

Water was added and the mixture separated into an aqueous phase and an organic phase. The organic phase was separated and dried with sodium sulfate.

The organic phase solvent (i.e., THF and hexanes) was exchanged with hexanes in an amount such that the final volume was concentrated to about 40 weight % of Kinetic EBI. The solution was cooled to −20° C. and filtered. The solid was dried to give a 35% yield of the kinetic isomer of EBI.

EXAMPLE 2 (PILOT PLANT)

23.8 kg of ethyl ether and 4.8 gal (1.25 eq.) of indene are charged to a clean, dry, first reactor. 10.2 kgs of indene are added. The pot temperature of the first reactor was lowered to −20° C. 37.3 kgs of butyllithium in hexanes were fed into the first reactor. The pot temperature was maintained below −10° C. during the feed. The reaction mixture was stirred out overnight at room temperature.

16.4 kg (87.3 moles) of dibromoethane was added to the first reactor. Upon completion of the dibromoethane addition, 3.8 kgs of THF were added. An exothermic reaction ensued. The reaction mixture was stirred out with nitrogen sweep.

25 kgs of the reactor medium were removed at atmospheric pressure. An equal amount of heptane was added back to the reactor to reach a pot temperature of about 95° C. The reaction mixture was then hot filtered through Celite at a temperature of 75° C. to 80° C. The cake was washed with 10 kgs of heptane, which was stripped to 3 to 4 gallons. The pot temperature was cooled, the reaction mixture filtered, and the product was isolated on a clear Buchner. Dry yield of EBI=6.3 kgs out of Buchner.

I claim:

1. A method for synthesizing hydrocarbyl bridged indene which comprises:
   (i) reacting indene with an alkali metal alkyl in a non-interfering solvent at a temperature below 0° C., wherein a first reaction mixture containing an alkali metal indenide and said solvent is produced;
   (ii) raising the temperature of said first reaction mixture to from 20° C. to 40° C.;
   (iii) combining said step (ii) first reaction mixture at 20° C. to 40° C. with a terminal dihalo alkane, wherein a second reaction mixture is produced and thereafter;
   (iv) adding tetrahydrofuran to said second reaction mixture wherein a third reaction mixture containing said hydrocarbyl bridged indene is produced;
   (v) adding water to said third reaction mixture, wherein an organic phase and an aqueous phase form;
   (vi) separating said step (v) aqueous and organic phases; and
   (vii) exchanging the solvent of said organic phase separated in step (v) with a hydrocarbon solvent from which said hydrocarbyl bridged indene is separated.

2. The method of claim 1 wherein said step (iii) terminal dihalo alkane has the formula XZX, in which X is any halogen and Z is —$(CH_2)_n$— (n=1–20).

3. A method for synthesizing 1,2-bis(indenyl)ethane which comprises:
   (i) reacting indene with an alkali metal alkyl in a non-interfering solvent at a temperature below 0° C., wherein a first reaction mixture containing an alkali metal indenide and said solvent is produced;
   (ii) raising the temperature of said first reaction mixture to from 20° C. to 40° C.;
   (iii) combining said step (ii) first reaction mixture at 20° C. to 40° C. with dibromoethane, wherein a second reaction mixture is produced and thereafter;
   (iv) adding tetrahydrofuran to said second reaction mixture wherein a third reaction mixture containing EBI is produced;
   (v) adding water to said third reaction mixture, wherein an organic phase and an aqueous phase form;
   (vi) separating said step (v) aqueous and organic phases; and
   (vii) exchanging the solvent of said organic phase separated in step (v) with a hydrocarbon solvent from which kinetic EBI is separated.

4. A method for synthesizing EBI which comprises:
   (i) reacting n-butyl lithium with indene at a temperature of 40° C. to 50° C. wherein a reaction mixture containing lithium indenide is produced;
   (ii) cooling said step (i) reaction mixture to −10C to −30° C.;
   (iii) adding dibromoethane to provide a second reaction mixture;
   (iv) adding tetrahydrofuran to said second reaction mixture at a temperature of −15° C. to −20° C. with agitation, wherein a third reaction mixture containing solid EBI a mother liquor is produced; and
   (v) separating solid EBI from said third reaction mixture, wherein a mother liquor solution of kinetic EBI is produced.

* * * * *